United States Patent
Chao et al.

(10) Patent No.: US 7,527,967 B2
(45) Date of Patent: May 5, 2009

(54) RECOMBINANT BACULOVIRUS AND VIRUS-LIKE PARTICLE

(75) Inventors: Yu-Chan Chao, Taipei (TW); Yen-Yen Liu, Taipei (TW)

(73) Assignee: Academia Sinica, Taipei (TW)

( * ) Notice: Subject to any disclaimer, the term of this patent is extended or adjusted under 35 U.S.C. 154(b) by 438 days.

(21) Appl. No.: 10/997,775

(22) Filed: Nov. 24, 2004

(65) Prior Publication Data

US 2005/0208066 A1    Sep. 22, 2005

Related U.S. Application Data

(60) Provisional application No. 60/525,092, filed on Nov. 25, 2003.

(51) Int. Cl.
*C12N 1/00* (2006.01)
*A61K 39/155* (2006.01)
*A61K 39/215* (2006.01)

(52) U.S. Cl. .............. 435/320.1; 424/211.1; 424/221.1

(58) Field of Classification Search ................ None
See application file for complete search history.

(56) References Cited

U.S. PATENT DOCUMENTS

| | | | | |
|---|---|---|---|---|
| 5,858,368 A | * | 1/1999 | Smith et al. | 424/192.1 |
| 6,001,806 A | * | 12/1999 | Hilbert et al. | 514/12 |
| 6,183,993 B1 | * | 2/2001 | Boyce et al. | 435/69.7 |
| 6,207,165 B1 | * | 3/2001 | Audonnet et al. | 424/199.1 |

OTHER PUBLICATIONS

Whitford et al. J. Virology, 1989, 63(3):1393-1399.*

Mayla Hsu et al. "Hepatitis C virus glycoproteins mediate pH-dependent cell entry of pseudotyped retroviral particles", PNAS 100(12):7271-7276, Jun. 10, 2003.

* cited by examiner

*Primary Examiner*—Stacy B Chen
(74) *Attorney, Agent, or Firm*—Occhiuti Rohlicek & Tsao LLP

(57) ABSTRACT

Recombinant baculoviruses, virus-like particles, and polypeptide that contain a protein sequence of a heterologous virus, related compositions, and related preparation, screening, delivery, detection, and treatment methods.

13 Claims, No Drawings

US 7,527,967 B2

RECOMBINANT BACULOVIRUS AND VIRUS-LIKE PARTICLE

RELATED APPLICATION

This application claims priority to U.S. Provisional Application Ser. No. 60/525,092, filed on Nov. 25, 2003, the contents of which is incorporated by reference in its entirety.

BACKGROUND

Virus is the cause of various disorders. For example, members of the coronavirus family cause hepatitis in mice, gastroenteritis in pigs, and respiratory infections in birds and humans. Among the more than 30 strains isolated so far, three or four infect humans. The severe acute respiratory syndrome (SARS), a newly found infectious disease, is associated with a novel coronavirus. This life-threatening respiratory coronavirus has touched off worldwide outbreaks in 2003. Vaccines and drugs against SARS coronavirus are vigorously sought. Nevertheless, the progress is rather slow due to safety concerns.

Baculoviruses, a group of insect-borne viruses, are safe for use in humans. They have been successfully used for generating active engineered protein in some mammalian cells. See, e.g., King et al., The Baculovirus Expression System: A Laboratory Guide; Chapman and Hall: London, 1992; Luckow, Curr. Opin. Biotechnol. 1993, 4, 564-572; O'reilly, et al., Baculovirus Expression Vectors: A Laboratory Manual, Oxford University Press: New York, 1994; and Smith et al., 1983, Mol. Cell Biol. 3, 2156-2165. On the other hand, as baculoviruses are quite different from coronaviruses and do not efficiently infect coronavirus target cells, their use in developing anti-coronavirus agents has been limited.

SUMMARY

This invention is based, at least in part, on the discovery that a heterologous viral polypeptide displayed on the surface of a recombinant baculovirus retains its activity, e.g., its immunogenicity. Further, a recombinant baculovirus displaying a surface protein of a coronavirus (CoV) or an influenza virus (IFV) mimics the corresponding virus to bind to and fuse with its target cell.

Accordingly, in one aspect, this invention features a recombinant baculovirus that contains a heterologous polypeptide displayed on the surface of the baculovirus. A "heterologous" polypeptide, nucleic acid, or gene refers to one that originates from a foreign species, or, if from the same species, is substantially modified from its original form. Examples of polypeptides heterologous to baculovirus include (1) a polypeptide of a different virus or (2) a fusion polypeptide having a baculovirus protein sequence, e.g., a baculoviral envelope-targeting sequence. Examples of a baculoviral envelope-targeting sequences include that of the carboxyl terminal amino acid (aa) 227-529 of baculovirus GP64 protein (SEQ ID NO: 9, shown below), or its functional equivalent.

```
                                      (SEQ ID NO: 9)
SMILKQKSTFTTRQIKAACLLIKDDKNNPESVTREHCLIDNDIYDLSKN

TWNCKFNRCIKRKVEHRVKKRPPTWRHNVRAKYTEGDTATKGDLMHIQE

ELMYENDLLKMNIELMHAHINKLNNMLHDLIVSVAKVDERLIGNLMNNS

VSSTFLSDDTFLLMPCTNPPAHTSNCYNNSIYKEGRWVANTDSSQCIDF

RNYKELAIHDVEFWIPTIGNTTYHDSWKDASGWSFIAQQKSNLITTMEN

TKFGGVGTSLSDITSMAEGELAAKLTSFMFGHVVNFVIILIVILFLYCM

IRNRNRQY.
```

A functional equivalent of a baculoviral envelope-targeting sequence refers to a polypeptide derived from a baculovirus surface protein, e.g., the GP64 protein. The derivative can be a fusion polypeptide or a polypeptide having one or more point mutations, insertions, deletions, truncations, or combination of the surface protein. It retains substantially the surface targeting ability of the surface protein, i.e., the ability to target itself to the envelope of a baculovirus.

In one embodiment, the above-mentioned heterologous polypeptide contains the sequence of a polypeptide of a heterologous virus (e.g., a coronavirus or an influenza virus). Examples of the heterologous polypeptide includes, but are not limited to, (1) the sequence of the envelope protein, membrane protein, nucleocapsid protein, or spike protein of a coronavirus (e.g., SARS CoV); (2) the sequence of hemagglutinin of influenza virus (e.g., influenza A virus or IAV); and (3) its antigenic fragment. Listed below are the full-length sequences of SARS CoV envelope protein, membrane protein, nucleocapsid protein, and spike protein; and IAV hemagglutinin.

```
SARS CoV envelope protein/GenBank
Accession No. AAP37020.1              (SEQ ID NO: 1)
MYSFVSEETGTLIVNSVLLFLAFVVFLLVTLAILTALRLCAYCCNIVNV

SLVKPTVYVYSRVKNLNSSEGVPDLLV

SARS CoV membrane protein/GenBank
Accession No. AAP37021.1              (SEQ ID NO: 2)
MADNGTITVEELKQLLEQWNLVIGFLFLAWIMLLQFAYSNRNRFLYIIK

LVFLWLLWPVTLACFVLAAVYRINWVTGGIAIAMACIVGLMWLSYFVAS

FRLFARTRSMWSFNPETNILLNVPLRGTIVTRPLMESELVIGAVIIRGH

LRMAGHSLGRCDIKDLPKEITVATSRTLSYYKLGASQRVGTDSGFAAYN

RYRIGNYKLNTDHAGSNDNIALLVQ

SARS CoV nucleocapsid protein/
GenBank
Accession No. AAP37024.1              (SEQ ID NO: 3)
MSDNGPQSNQRSAPRITFGGPTDSTDNNQNGGRNGARPKQRRPQGLPNN

TASWFTALTQHGKEELRFPRGQGVPINTNSGPDDQIGYYRRATRRVRGG

DGKMKELSPRWYFYYLGTGPEASLPYGANKEGIVWVATEGALNTPKDHI

GTRNPNNNAATVLQLPQGTTLPKGFYAEGSRGGSQASSRSSSRSRGNSR

NSTPGSSRGNSPARMASGGGETALALLLLDRLNQLESKVSGKGQQQQGQ

TVTKKSAAEASKKPRQKRTATKQYNVTQAFGRRGPEQTQGNFGDQDLIR

QGTDYKHWPQIAQFAPSASAFFGMSRIGMEVTPSGTWLTYHGAIKLDDK

DPQFKDNVILLNKHIDAYKTFPPTEPKKDKKKKTDEAQPLPQRQKKQPT

VTLLPAADMDDFSRQLQNSMSGASADSTQA
```

```
SARS CoV spike protein/GenBank Accession No. AAP37017.1:    (SEQ ID NO: 4)
MFIFLLFLTLTSGSDLDRCT TFDDVQAPNYTQHTSSMRGV YYPDEIFRSDTLYLTQDLFL

PFYSNVTGFHTINHTFGNPV IPFKDGIYFAATEKSNVVRG WVFGSTMNNKSQSVIIINNS

TNVVIRACNFELCDNPFFAV SKPMGTQTHTMIFDNAFNCT FEYISDAFSLDVSEKSGNFK

HLREFVFKNKDGFLYVYKGY QPIDVVRDLPSGFNTLKPIF KLPLGINITNFRAILTAFSP

AQDIWGTSAAAYFVGYLKPT TFMLKYDENGTITDAVDCSQ NPLAELKCSVKSFEIDKGIY

QTSNFRVVPSGDVVRFPNIT NLCPFGEVFNATKFPSVYAW ERKKISNCVADYSVLYNSTF

FSTFKCYGVSATKLNDLCFS NVYADSFVVKGDDVRQIAPG QTGVIADYNYKLPDDFMGCV

LAWNTRNIDATSTGNYNYKY RYLRHGKLRPFERDISNVPF SPDGKPCTPPALNCYWPLND

YGFYTTTGIGYQPYRVVVLS FELLNAPATVCGPKLSTDLI KNQCVNFNFNGLTGTGVLTP

SSKRFQPFQQFGRDVSDFTD SVRDPKTSEILDISPCSFGG VSVITPGTNASSEVAVLYQD

VNCTDVSTAIHADQLTPAWR IYSTGNNVFQTQAGCLIGAE HVDTSYECDIPIGAGICASY

HTVSLLRSTSQKSIVAYTMS LGADSSIAYSNNTIATPTNF SISITTEVMPVSMAKTSVDC

NMYICGDSTECANLLLQYGS FCTQLNRALSGIAAEQDRNT REVFAQVKQMYKTPTLKYFG

GFNFSQILPDPLKPTKRSFI EDLLFNKVTLADAGFMKQYG ECLGDINARDLICAQKFNGL

TVLPPLLTDDMIAAYTAALV SGTATAGWTFGAGAALQIPF AMQMAYRFNGIGVTQNVLYE

NQKQIANQFNKAISQIQESL TTTSTALGKLQDVVNQNAQA LNTLVKQLSSNFGAISSVLN

DILSRLDKVEAEVQIDRLIT GRLQSLQTYVTQQLIRAAEI RASANLAATKMSECVLGQSK

GVVFLHVTYVPSQERNFTTA PAICHEGKAYFPREGVFVFN GTSWFITQRNFFSPQIITTD

NTFVSGNCDVVIGIINNTVY DPLQPELDSFKEELDKYFKN HTSPDVDLGDISGINASVVN

IQKEIDRLNEVAKNLNESLI DLQELGKYEQYIKWPWYVWL GFIAGLIAIVMVTILLCCMT

SCCSCLKGACSCGSCCKFDE DDSEPVLKGVKLHYT*
```

```
IAV hemagglutinin                    (SEQ ID NO: 10)
MGKIVLFLSIASLVNSDKICIGYHANNSTAKVDTIMEKNVTVTHAKDIPE

KKHNGKLCGLNGVKPLILRDCSVAGWLLGNPMCDEFLMVPEWSYIVEKNN

PVNGLCYPGDFQDYEELKHLLSSTTHFEKIQMFPRNSWPQHDTSGVTAAC

PFNGKSSFFRNMVWLIKKNNEYLTIKRGYKNTNQEDLLIMWGIHHPSHDE

EQVRLYKNPRTYISVGTSTLNQRLSPIIAERPQVNGQSGRMSFYWTILKP

SDTINFETNGNFIPPEYAFKIVKKGDSAIIRSELEYGNCNTRCQTPMGAL

NSSMPFQNIHPITIGECPKYVKSNRLVLATGLRNIPQIETRGLFGAIAGF

IEGGWQGMVDGWYGYHHSNDQGSGYAADKESTQRAIDGITNKVNSIIDKM

NTQFEAVGKEFNNLERRIGNLNKKMEDGFLDIWTYNAELLVLMENERTLD

LHDSNVKNLYEKVRLQLKDNAKELGNGCFEFHHKCDNECMESVKNGTYNY

PHYSEEARLKREEISGVKLESIGTYQILSIYSTVASSLVLAIMIAGLSFW

MCSNGSLQCRICI
```

Examples of an antigenic fragment of the SARS CoV spike protein include, but are not limited to, aa 17-510, aa 17-763, 17-966, and 510-763 of SEQ ID NO: 4 (SEQ ID NOs: 5-8, respectively).

The invention further features a recombinant virus-like particle that contains the envelope protein and the membrane protein of a coronavirus, such as those of SARS CoV described above (SEQ ID NOs: 1 and 2, respectively). A "virus-like-particle" refers to a protein complex that contains a protein of a virus and resembles, in shape, the virus. This protein complex lacks the intact genome, and one or more other proteins of that virus. In one example, the virus-like particle further contains the spike protein of the coronavirus or its antigenic fragment, e.g., one of SEQ ID NOs: 4-8 described above. One can make the recombinant virus-like particle by (1) introducing into a host cell a first nucleic acid encoding the envelope protein or the membrane protein of a coronavirus (e.g., SARS CoV), (2) culturing the host cell in a medium under conditions permitting generation of the recombinant virus-like particle, and (3) purifying the recombinant virus-like particle. In one embodiment, a second nucleic acid encoding the spike protein of the coronavirus or its antigenic fragment is also introduced into the host cell.

The invention also features an isolated recombinant polypeptide that contain (i) a baculoviral envelope-targeting sequence (e.g., SEQ ID NO: 9) or its functional equivalent, and (ii) a heterologous sequence. Examples of the heterologous sequence include, but are not limited to, the envelope protein, membrane protein, nucleocapsid protein, or spike protein of a coronavirus (e.g., SEQ ID NOs: 1-8) or its antigenic fragment; and the sequence of hemagglutinin of an influenza virus or its antigenic fragment. One can generate the recombinant polypeptide by (1) introducing an expression vector encoding the polypeptide into a host cell, (2) culturing the host cell in a medium under conditions permitting expression of the polypeptide, and (3) purifying the polypeptide.

A "vector" refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. The term "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of transcription of RNA desired, and the like.

The above-described recombinant baculovirus, recombinant virus-like particle, or recombinant polypeptide can be used to generate an antibody or an immune response against a heterologous protein or a virus (e.g., SARS CoV or IFV) in a human or non-human subject. Thus, also within the scope of this invention is an immunogenic composition, e.g., a vaccine, containing the recombinant baculovirus, recombinant virus-like particle, or isolated recombinant polypeptide, and a pharmaceutically acceptable carrier. By administering to a subject the composition, one can induce in the subject an antibody or an immune response against the heterologous protein or virus.

In addition to generating antibodies, the above-described recombinant baculovirus, recombinant virus-like particle, or recombinant polypeptide can also be used to screen compounds that bind to a virus (e.g. a coronavirus or a influenza virus) or a protein thereof. Such compounds are candidates for treating an infection with the virus.

Accordingly, the invention features a method of identifying a molecule that binds to a virus. The method includes (1) providing a first recombinant baculovirus that contains a heterologous polypeptide having a sequence of a protein of the virus; (2) contacting a molecule with the first recombinant baculovirus; and (3) detecting a binding between the first recombinant baculovirus and the molecule. The molecule is determined to be able to bind to the virus if it binds to the first recombinant baculovirus, but not to a second baculovirus that is identical to the first recombinant baculovirus, except that the polypeptide in the second baculovirus does not have the sequence of the protein of the virus. In a preferred embodiment, the first recombinant baculovirus contains a fusion polypeptide having a baculoviral envelope-targeting sequence (e.g., SEQ ID NO: 9, or its functional equivalent) fused to the sequence of the spike protein of the virus or its fragment (e.g., one of SEQ ID NOs: 4-8).

The invention also features a method of identifying a molecule that binds to a coronavirus. The method includes (1) providing a first recombinant polypeptide that contains the sequence of the envelope protein, membrane protein, nucleocapsid protein, or spike protein of a coronavirus; (2) contacting a molecule with the first recombinant polypeptide; and (3) detecting a binding between the first recombinant polypeptide and the molecule. The molecule is determined to be able to bind to the coronavirus if it binds to the first recombinant polypeptide, but not to a second polypeptide that is identical to the first recombinant polypeptide, except that the second polypeptide does not contain the sequence of the envelope protein, membrane protein, nucleocapsid protein, or spike protein of the coronavirus. Preferably, the first recombinant polypeptide is a fusion polypeptide having (1) SEQ ID NO: 9 and (2) the sequence of the spike protein of the virus or its fragment, e.g., SEQ ID NO: 4, 5, 6, 7, or 8.

The invention further features a method of identifying a molecule that binds to a particular viral protein of interest. The method includes providing a first recombinant virus-like particle that contains a polypeptide having a sequence the protein; contacting a molecule with the first recombinant virus-like particle; and detecting a binding between the first recombinant virus-like particle and the molecule. The molecule is determined to be able to bind to the protein if it binds to the first recombinant virus-like particle, but not to a second virus-like particle that is identical to the first recombinant virus-like particle, except that the polypeptide in the second virus-like particle does not contain the sequence of the protein of the virus.

In the above-described three methods, examples of the molecule to be identified include small inorganic molecules, small organic molecules, nucleic acids, or proteins. It is known that a virus infects its target cell by binding to a receptor located on the cell, fusing with the cell, and transferring its genome and certain proteins into the cell. Accordingly, a cell surface protein identified by the above-described three methods is a candidate of a cell-surface receptor of the virus. Thus, the above-described three methods can be used to identify such a receptor.

Similarly, the methods can be used to identifying a target cell of the virus. For example, a cell expressing the just-mentioned candidate cell-surface protein is a candidate target cell of the virus. Alternatively, one can identify a target cell of the virus by the three methods described below.

The first method includes (1) providing a first recombinant baculovirus of this invention that contains a heterologous polypeptide having the sequence of a protein of a virus; (2) contacting the first recombinant baculovirus with a cell; and (3) detecting a binding between the first recombinant baculovirus and the cell. The cell is determined to be a target cell of the virus if the cell binds to the first recombinant baculovirus, but not to a second baculovirus that is identical to the first recombinant baculovirus, except that the second baculovirus does not contain the heterologous polypeptide.

The second method includes (1) providing a first recombinant virus-like particle of this invention that contains a polypeptide having a sequence of a protein of a virus; (2) contacting the first recombinant virus-like particle with a cell; and (3) detecting a binding between the first recombinant virus-like particle and the cell. The cell is determined to be a target cell of the virus if the cell binds to the first recombinant virus-like particle, but not to a second virus-like particle that is identical to the first recombinant virus-like particle, except that the polypeptide in the second virus-like particle does not contain the sequence of the protein of the virus.

The third method includes (1) providing a first recombinant polypeptide of this invention that contains the sequence of the envelope protein, membrane protein, nucleocapsid protein, or spike protein of a coronavirus; (2) contacting the first recombinant polypeptide with a cell; and (2) detecting a binding between the first recombinant polypeptide and the cell. The cell is determined to be a target of the coronavirus if the cell binds to the first recombinant polypeptide, but not to a second polypeptide that is identical to the first recombinant polypeptide, except that the second polypeptide does not contain the sequence of the envelope protein, membrane protein, nucleocapsid protein, or spike protein of the coronavirus.

In preferred embodiments of just-described methods, the viral proteins contain (1) the sequence of the coronavirus spike protein or its antigenic fragment, such as SEQ ID NOs:

4-8; or (2) the sequence of the influenza virus hemagglutinin, such as SEQ ID NO: 10, or its antigenic fragment. Any identified cells can be further validated in the manner described in the examples below.

Still within the scope of this invention is a method of identifying a compound for treating an infection with a virus. The method includes providing a first cell that binds to the virus, e.g., a Vero E6 (Drosten et al., 2003, N. Engl. J. Med. 348:1967-1976; and Ksiazek et al., 2003, N. Engl. J. Med 348:1953-1966.), HFL 1 (ATCC CCL-153), NCI-H520 (ATCC HTB-182), A-549 (ATCC CCL-185), or MRC-5 (ATCC CCL-171) cell; and providing a recombinant baculovirus, virus-like particle, or polypeptide of this invention; (2) incubating the first cell and the recombinant baculovirus, virus-like particle, or polypeptide in a medium containing a compound; and (3) determining a level of the binding between the first cell and the recombinant baculovirus, virus-like particle, or polypeptide. The compound is determined to be effective in treating the infection if the level of the binding is lower than that determined in the same manner from a second cell except that the second cell is incubated in a medium free of the compound. In one embodiment, when using the recombinant baculovirus, the infection of the cell by the baculovirus is examined. The compound is determined to be effective in treating the infection if the level of the infection is lower than that determined in the same manner from a second cell except that the second cell is incubated in a medium free of the compound.

As mentioned above, a virus binds to and transfers its genome and protein into a target cell. Accordingly, a further aspect of this invention features a method of introducing an agent into a target cell, such as a eukaryotic cell. The method includes (1) providing a recombinant baculovirus of this invention that contains an agent of interest and a heterologous polypeptide, such as one of SEQ ID NOs: 1-8 and 10 or its functional equivalent, that binds to a cell; and (2) contacting the recombinant baculovirus with a cell. The recombinant baculovirus binds to and fuses with the cell, thereby introducing the agent into the cell. Examples of the agent include nucleic acid and protein. The term "nucleic acid" refers to DNA molecules (e.g., a cDNA or genomic DNA), RNA molecules (e.g., an interference RNA, mRNA, and anti-sense RNA), and analogs of the DNA or RNA. A DNA or RNA analog can be synthesized from nucleotide analogs. The nucleic acid molecule can be single-stranded or double-stranded. The nucleic acid can be operatively linked to suitable regulatory sequences to form a vector. In a preferred embodiment, the nucleic acid is or encodes an interference RNA (iRNA), which targets a segment of a viral gene essential to a viral infection and represses the expression of the gene, thereby inhibiting the infection with the virus.

Thus, the invention features a double-stranded nucleic ribonucleic acid (dsRNA) that contains two stands. The first strand is substantially identical to 19-49 consecutive nucleotides of SEQ ID NO: 12 listed in Example 1 below. That is, it is at least 70% (i.e., any percentage between 70% and 100%) identical to those consecutive nucleotides. The second strand of the dsRNA is complementary to the first strand. This dsRNA inhibits the expression of the replicase of a coronavirus, i.e., it reduced the level of replicase protein or RNA level in a statistically significant manner.

The "percent identity" of two nucleic acids or of two amino acid sequences is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In one example, the above-described dsRNA contains a first strand that is complementary to one of SEQ ID NOs: 12-18 listed in Example 1 below, or the complement thereof. The dsRNA can be made from a nucleic acid. Thus, within the scope of this invention is a nucleic acid containing an expression control sequence operatively linked to a nucleotide sequence that is a template for one or both strands of the dsRNA described above.

Also within the scope of this invention is a pharmaceutical composition containing a compound identified by the screening methods described above or an RNAi agent (e.g., a dsRNA or a vector encoding such dsRNA), and a pharmaceutically acceptable carrier. A method of treating an infection with a coronavirus is also featured. The method includes administering to a subject in need thereof an effective amount of a compound or RNAi agent of this invention.

This invention further features a method of detecting a viral-neutralizing activity of a sample, such as that of an antiserum or an antibody preparation. The method includes (1) incubating a first medium that contains a recombinant baculovirus of this invention with a sample; and (2) determining the ability of the recombinant baculovirus in the incubated first medium to infect host cells, e.g., Vero E6, HFL 1, NCI-H520, A-549, or MRC-5 cells. The sample is determined to have a viral-neutralizing activity if the ability of the recombinant baculovirus in the incubated first medium to infect host cells is lower than that determined in the same manner from a second medium except that the second medium is not incubated with the sample.

Finally, the invention features a baculovirus that is resistant to the complement C system of a mammal and a method of preparing such a baculovirus. The method includes introducing into a baculovirus a polypeptide having the sequence of one of SEQ ID NOs: 1-8. It was unexpected that the baculovirus described herein is resistant to the complement C system, as other baculovirus would normally be killed by the complement C system. Due to this resistance, the baculovirus, once introduced into a mammal, maintain its structure and activity better than the others and is therefore superior to the others in delivering agents, e.g., protein or nucleic acid, into a mammal, including a human.

The details of one or more embodiments of the invention are set forth in the accompanying description below. Other advantages, features, and objects of the invention will be apparent from the detailed description and the claims.

DETAILED DESCRIPTION

This invention relates to recombinant baculoviruses, virus-like particles, and polypeptides, and their use in treating an infection with virus, such as SARS.

The recombinant baculoviruses of this invention display heterologous polypeptide sequences on their surfaces and have several unexpected advantages over conventional baculoviruses. For example, a displayed heterologous polypeptide unexpectedly retains its activity, such as allowing the recombinant baculoviruses to bind to target cells of a heterologous virus. The recombinant baculoviruses therefore are useful in delivering agents, such as therapeutic dsRNA, to these target cells. Also, as the heterologous polypeptide displayed on the baculoviruses retains its antigenicity, the recombinant baculoviruses can be used to make an immunogenic composition for generating antibodies against the heterologous virus in a subject. Further, the recombinant baculoviruses are resistant to the complement C system. They therefore can be safely administered to the subject by standard techniques.

To produce the recombinant baculoviruses, one can co-transfect suitable host cells with a linearized baculoviral DNA and an expression vector encoding a heterologous protein to be displayed in the manner described in Example 1 below or by other standard techniques. See, e.g., Pfeifer et al., 1997, Gene 188:183-190; and Clem et al., 1994, J. Virol. 68:6759-6762. Suitable host cells may vary depending on system design or specificity consideration. Examples of suitable host cells include, but are not limited to, the cells derived from species ranging from insects to vertebrates. Preferred host cells are insect-derived cells and mammalian cells. Examples of the insect-derived cells include S2 cells, Kc cells, and C6/36 cells. Suitable mammalian cells include primary cells or cell lines from murine, rat, rabbit, porcine, or human sources. Once expressed in the host cells, baculovirus particles are formed from baculoviral proteins encoded by the baculoviral DNA and the heterologous protein.

In one example, to display a heterologous polypeptide, one can make a fusion protein of the heterologous polypeptide and a baculoviral envelope-targeting sequence, e.g., baculovirus GP64 protein, or its functional equivalent, using standard recombinant techniques. GP64, the major glycoprotein in the envelope of a budding baculovirus, is involved in binding of a baculovirus to an insect host cell (Hefferon et al., 1999, Virology 258:455-468.). In one embodiment, the C-terminal membrane-anchoring domain of GP64 (aa 227-529) is fused to a N-terminal segment of a coronavirus spike protein. The resultant fusion protein attaches tightly onto the surface of baculovirus. In another embodiment, the heterologous protein, without being fused to any baculovirus protein sequence, is displayed onto the surface of a baculovirus.

The recombinant virus-like particles and polypeptides of this invention can also be produced using the just-described systems. In particular, to make the virus-like particles, one can co-infect into suitable host cells a linearized baculoviral DNA and nucleic acids encoding the envelope and membrane proteins of a heterologous virus, such as coronavirus and influenza virus. These proteins, once expressed, aggregate to form the virus-like particles.

It is known that various viral and non-viral proteins specifically bind to receptors on certain eukaryotic cells. Examples of these viral proteins include spike and hemagglutinin proteins. Examples of non-viral proteins include antibodies, protein ligands to the receptors (e.g., growth factors and cytokines), and extracellular matrix components. If these receptor-binding proteins are co-expressed with a heterologous polypeptide in the baculovirus host cells of this invention, the resultant recombinant baculovirus or virus-like particles of this invention contain these proteins and acquire the ability to specifically bind to the receptors. As a result, they can be used as a vehicle to deliver an agent of interest to eukaryotic cells, including normal human cells (e.g., antigen presenting cells) and diseased cells (e.g., virus infected cells and tumor cells). The agent can be a therapeutic protein, such as a vaccine, an antibody, a biologically active peptide (e.g., a toxin), a cytokine, a cytokine receptor, a growth factor, a growth factor receptor, or an enzyme. It can also be a nucleic acid. Examples of the protein include. Examples of the nucleic acid, such as a dsRNA, a ribozyme, or an analog or derivative of a dsRNA or a ribozyme.

In preferred embodiments, coronavirus spike protein and IFV hemagglutinin are expressed and incorporated into the recombinant baculovirus or virus-like particles of this invention.

Spike protein, the outermost component of coronavirus membrane protein, plays two important roles: (1) binding to a specific cell surface receptor(s) of host cells, and (2) inducing membrane fusion, thereby allowing viral entry into the cells. It is the primary target for the host's immune responses since, in an animal, antibodies against a coronavirus are induced mainly by the spike protein (see Lai and Cavanagh, 1997, Adv. Virus Res. 48: 1-101).

Hemagglutinin (HA), an integral membrane protein homotrimer on the surface of influenza virus (e.g., IAV), is the most important determinant of pathogenicity in influenza virus (Webster et al., 1987, Cell, 50, 665-666.). It governs IAV host recognition and entry, and is activated through protease cleavage, which divides the protein into two sub-fragments, HA1 and HA2, connected by a disulfide bond. This cleavage is a prerequisite for IAV infection. The protease cleavage mostly occurs on the surface of host cells (by, e.g., a trypsin-like protease). In the highly pathogenic strain of the IAV, the HA1-HA2 boundary contains multiple basic amino acids (e.g. RKRKKR), which can be cleaved by a ubiquitous protease. The cleaved HA causes respiratory illness.

As both the spike protein and HA are antigenic, one can use them as immunogenic compositions or vaccines to generate antibodies and immune responses in a subject against infections with coronavirus (e.g., SARS) and influenza virus (e.g., flu). Nonetheless, large-scale production of vaccines against SARS CoV or IAV H5 subtypes (e.g., H5N1 and H5N2) is limited since high-level biocontainment facilities and trained personnel are required. It is also limited due to inability to obtain high yields of virus from embryonated chickens' eggs. As this recombinant baculoviruses, virus-like particles of this invention, and polypeptide of this invention do not involve any pathogenic virus itself, they can be safely used to produce a large amount of immunogenic compositions.

Thus, within the scope of this invention is an immunogneic or antigenic composition that contains a pharmaceutically acceptable carrier and an effective amount of a recombinant baculovirus, virus-like particle, or polypeptide of this invention. The carriers used in the composition are selected on the basis of the mode and route of administration, and standard pharmaceutical practice. Suitable pharmaceutical carriers and diluents, as well as pharmaceutical necessities for their use, are described in Remington's Pharmaceutical Sciences. An adjuvant, e.g., a cholera toxin, *Escherichia coli* heat-labile enterotoxin (LT), liposome, or immune-stimulating complex (ISCOM), can also be included in the composition, if necessary. Various adjuvants that can be used to increase the immunological response depend on the host species and include Freund's adjuvant (complete and incomplete), mineral gels such as aluminum hydroxide, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

The amount of a composition administered will depend, for example, on the particular peptide antigen in the composition, whether an adjuvant is co-administered with the antigen, the type of adjuvant co-administered, the mode and frequency of administration, and the desired effect (e.g., protection or treatment), as can be determined by one skilled in the art. In general, the recombinant baculovirus, virus-like particles body, or polypeptide is administered in amounts ranging between 1 μg and 100 mg per adult human dose. If adjuvants are co-administered, amounts ranging between 1 ng and 1 mg per adult human dose can generally be used. Administration is repeated as necessary, as can be determined by one skilled in the art. For example, a priming dose can be given to a subject followed by three booster doses at weekly intervals. A booster shot can be given at 8 to 12 weeks after the first administration, and a second booster can be given at 16 to 20 weeks, using the same formulation. Sera can be taken from the subject for testing the immune response or antibody production elicited by the composition against the antigen. Methods of assaying antibodies against a specific antigen are well known in the art. Additional boosters can be given as needed. By varying the amount of the composition and frequency of administration, the protocol can be optimized for eliciting a maximal production of the antibodies.

The above-described recombinant baculoviruses, virus-like particles, and polypeptides can be used to identify a molecule that binds to a virus, a cellular receptor for the virus, and a target cell for the virus. More specifically, they can be incubated with a test molecule, a test polypeptide, or a test cell. One can then detect, using standard techniques, the binding between each of them and the test molecule, polypeptide, or cell. The molecule, polypeptide, and cell are determined to be able to bind to the virus, a receptor for the virus, or the target cell for the virus, respectively, if they specifically bind to the baculoviruses, virus-like particles, or polypeptides, but not to controls.

The assay can be conducted in the manner described in the example below or in a variety of ways known in the art. For example, one method involves anchoring the recombinant baculoviruses/virus-like particles/polypeptides (or the test molecule/polypeptide/cell) onto a solid phase and detecting a complex formed by anchor and non-anchor components on the solid phase at the end of the reaction. In practice, microtiter plates may conveniently be utilized as the solid phase. The anchor component may be immobilized by non-covalent or covalent attachments. Non-covalent attachment may be accomplished by simply coating the solid surface with a solution of the anchor component and drying the plates. Alternatively, an immobilized antibody (e.g., a monoclonal antibody) specific for the anchor component may be used to immobilize the anchor component to the solid surface. The non-anchor component is added to the solid surface coated with the anchor component. After the reaction is complete, unbound fraction of the non-anchor components is removed (e.g., by washing) under conditions such that any complexes formed remain immobilized on the solid surface. Detection of these complexes can be accomplished in a number of ways. Where the non-anchor component is pre-labeled, detection of the label immobilized on the solid surface indicates that complexes were formed. Where the non-anchor component is not pre-labeled, an indirect label can be used to detect complexes formed on the surface, e.g., using an antibody specific for the non-anchor component (the antibody, in turn, may be directly labeled or indirectly labeled with a labeled anti-Ig antibody).

Alternatively, the reaction can be conducted in a liquid phase. The complexes are separated from unbound components, e.g., using an immobilized antibody specific for the recombinant baculoviruses/virus-like particles/polypeptides or the test molecule/polypeptide/cell. The complexes are then detected, e.g., using a labeled antibody specific for the other component.

A test molecule, a test polypeptide, and a test cell thus identified are a drug candidate for treating a viral infection, a receptor for the virus, and a target cell of the virus, respectively. The molecule, as well as a soluble form of the polypeptide, can be further validated by ascertaining its ability to treat the infection, e.g., to inhibit the binding of a coronavirus to its target cells, using standard techniques or in the same manner described in Example 1 below.

The invention further features a method for identifying a compound for treating an infection with a virus based on inhibition of a virus' binding to its target cell. More specifically, a virus target cell is incubated with a compound in the presence of a recombinant baculovirus, virus-like particle, or polypeptide of this invention. The binding level between the cell and the recombinant baculovirus, virus-like particle, or polypeptide is then determined. A decrease in the binding level indicates that the compound inhibits the binding of the virus to its target cell, thereby confirming its efficacy in treating the infection.

The above-mentioned molecule or compound can be obtained from compound libraries, such as peptide libraries or peptoid libraries. The libraries can be spatially addressable parallel solid phase or solution phase libraries. See, e.g., Zuckermann et al. J. Med. Chem. 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993; Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222:301-310, 1991; and U.S. Pat. No. 5,223,409).

Besides the above-described molecule or compound, also within the scope of this invention is a dsRNA that inhibits the expression of a viral gene via RNA interference. RNA interference (RNAi) is a process in which dsRNA directs homologous sequence-specific degradation of messenger RNA. In mammalian cells, RNAi can be triggered by 21-nucleotide duplexes of small interfering RNA (siRNA) without activating the host interferon response. As this process represses the expression of a viral gene in the cells, it can be used to treat an infection with a virus. One can determine which viral gene to target based on whether a protein encoded by a viral gene plays a role in an infection or in the corresponding pathogenesis. In general, valid targets are genes required for viral replication, viron formation, binding to or entering target cells, or pathogenesis of the infection or the associated disorders. One example is SRAS CoV replicase gene.

The dsRNA of this invention can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

The dsRNA or vector of this invention can be delivered to a virus target cell by methods, such as that described in Akhtar et al., 1992, Trends Cell Bio. 2, 139. For example, it can be introduced into cells using liposomes, hydrogels, cyclodextrins, biodegradable nanocapsules, or bioadhesive microspheres. Alternatively, the dsRNA or vector can be locally delivered by direct injection or by use of an infusion pump. Other approaches include employing various transport and carrier systems, for example through the use of conjugates and biodegradable polymers.

The above-described compounds and dsRNA can be used for treating viral infection, such as SARS. The invention therefore features a method of treating such an infection, e.g., by administering to a subject in need thereof an effective amount of a compound or dsRNA of the invention. Subjects to be treated can be identified as having, or being at risk for acquiring, a condition characterized by the infection. This method can be performed alone or in conjunction with other drugs or therapy. The term "treating" is defined as administration of a composition to a subject with the purpose to cure, alleviate, relieve, remedy, prevent, or ameliorate a disorder, the symptom of the disorder, the disease state secondary to the disorder, or the predisposition toward the disorder. An "effective amount" is an amount of the composition that is capable of producing a medically desirable result, e.g., as described above, in a treated subject.

In one in vivo approach, a therapeutic composition (e.g., a composition containing an RNAi agent or a compound of the invention) is administered to a subject. Generally, the agent or the compound is packed in a recombinant baculovirus or virus-like particle. It can also be suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 mg/kg. Wide variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

Also within the scope of this invention is a pharmaceutical composition that contains a pharmaceutically acceptable carrier and an effective amount of an RNAi agent or a compound of the invention. The pharmaceutical composition can be used to treat SARS. The pharmaceutically acceptable carrier includes a solvent, a dispersion medium, a coating, an antibacterial and antifungal agent, and an isotonic and absorption delaying agent.

A pharmaceutical composition of the invention can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the composition with a solid carrier and a lubricant. Examples of solid carriers include starch and sugar bentonite. The composition can also be administered in a form of a hard shell tablet or a capsule containing a binder, e.g., lactose or mannitol, a conventional filler, and a tableting agent. The pharmaceutical composition can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

The efficacy of a composition of this invention can be evaluated both in vitro and in vivo. Based on the results, an appropriate dosage range and administration route can be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Construction of Vectors

The coding sequence of EGFP and a SV40 poly(A) termination signal originally derived from the plasmid pEGFP-C1 (Clontech) were inserted into the pTriEx-3 transfer vector (Novagen) at the NcoI and HindIII restriction sites within the multiple cloning sites (MCS) to generate a reporter vector. The resultant pTpcE plasmid contained the EGFP gene under the control of both p10 and CMV promoters, and expressed EGFP in both insect and mammalian cells.

The signal sequence (SS) of the AcMNPV gp64 gene was amplified from purified wild-type AcMNPV genomic DNA to generate vectors encoding fusion proteins containing a GP64 fragment. The oligonucleotide primers used are shown below:

```
GPSF:
5'-AGGCCTCAATGCTACTAGTAAATC-3'        (SEQ ID NO:12)
and

GPSR2:
5'-GGCCGCAAAGGCCGAATGCGCCGC-3'        (SEQ ID NO:13).
```

The C-terminal (CT) of the gp64 gene (encoding amino acid residues 227-529) was amplified using GPCF227: 5'-GGCCACGGTGGCTATGATTCTCAAACAAAAGTC-3' (SEQ ID NO:20) and GPCR: 5'-CCCGGGTTAATAT-TGTCTATTACG-3' (SEQ ID NO:21). Both the SS and CT fragments were first cloned into the pZeroBlunt vector (Invitrogen) and then cloned sequentially into the PstI/KpnI and KpnI/SmaI sites of the pBacPAK8 transfer vector (Clontech), under the control of a polyhedrin promoter. The polyhedrin promoter plus the gp64 gene segment and a poly(A) termination signal were cleaved out using the EcoRV and HindIII restriction sites and ligated into the PvuII and HindIII sites of the pTpcE plasmid to create the pTpcEpG plasmid. As both GPSR2 and GPCF227 primers contain SfiI sites (GGCCN4NGGCC), one cut from this restriction enzyme allowed the pTpcEpG plamid to accept inserts with compatible ends.

Gene fragments encoding various C-terminal truncations of the SARS CoV spike protein (minus the signal sequence)

were amplified by PCR from a full-length spike clone. An S510 fragment (encoding residues 17-510) was amplified using the SpikeF2 (5'-GGCCTTTGCGGCCGACCGGTG-CACCACTTTTG-3' (SEQ ID NO:22)) and SpikeR510 (5'-GGCCACCGTGGCCGGTGCATTTAAAAG-3' (SEQ ID NO:23)) primers. An S763 fragment (encoding residues 17-763) was amplified using the SpikeF2 and SpikeR763 (5'-GGCCACCGTGGCCACTTCACGTGTGTTGCGATC-3' (SEQ ID NO:24)) primers. An S966 fragment (encoding residues 17-966) was amplified using the SpikeF2 and SpikeR966 (5'-GGCCACCGTGGCCAGTCGCGAAAG-GATGTCATTTAGCAC-3' (SEQ ID NO:25)) primers. All of the three PCR products were first cloned into pZeroBlunt, then cut with SfiI restriction enzyme and inserted into SfiI-cut pTpcEpG vectors, to form pTpcEpGS510, pTpcEpGS763, and pTpcEpGS966, respectively. All these vectors contain both the sequence encoding the signal sequence and the sequence encoding the residues 227-529 of AcMNPV gp64.

Generation of Baculoviruses, Virus-Like Particles, and SARS CoV Proteins

*Spodoptera frugiperda* IPLB-Sf21 (Sf21) cell line was cultured at 26° C. in a TNM-FH insect medium, supplemented with 8% heat-inactivated fetal bovine serum (FBS). The cell line was used for the propagation and infection of wild type and recombinant AcMNPV. The just-described plasmids pTpcE, pTpcEpGS510, pTpcEpGS763, and pTpcEpGS966 were cotransfected with vAcRP23.Laz (PharMingen), a linearized viral DNA of AcMNPV, into Sf21 cells using Lipofectin (Life Technologies) to produce the recombinant baculoviruses vAtEG, vAtEGp64S5 10, vAtEGp64S763, and vAtEGp64S966, respectively.

Western blot analysis was conducted to detect the expression of the GP64-spike fusion proteins encoded by these vectors. Sf21 cells were infected with vAtEG, vAtEGp64S510, vAtEGp64S763 and vAtEGp64S966 at multiplicity of infection (moi) of 5. Four days later, total proteins were prepared from the cells and separated on 5% SDS polyacrylamide gels. The proteins were transferred onto PVDF membrane (Millipore) and probed with a rabbit polyclonal anti-Spike antibody (1:10000 dilution), followed by incubating with a secondary antibody (Goat anti-rabbit IgG-HRP, at 1:3000 dilution). The proteins were visualized by ECL chemiluminiscence. The results showed that various GP64-spike proteins were expressed in the cells. The envelope, membrane, and nucleocapsid proteins of SARS CoV were also successfully generated using corresponding recombinant baculoviruses in the same manner.

To observe the virus-like particles, an electron microscopy was conducted. More specifically, supernatants were harvested from Sf21 cells culture four days after the cells had been infected with baculovirus containing the corresponding coding sequences. The supernatants were then centrifuged at 300 rpm for 10 minutes to remove cell debris, and filtered through a 0.45 µM filter. The filtrates were loaded onto a 24 well plate containing electron microscopy (EM) copper grids and spun for 33 minutes at 3000 rpm. The grids were negatively stained and observed under an electron microscope. It was found that the co-expression of the envelope and membrane proteins, or the envelope, membrane, and spike proteins resulted in virus-like particles in the host cells.

The virus-like particles, containing spike protein, can serve as a "native" vaccine for generating antibody in a subject. In addition, as these virus-like particles bind to target cells of SARS CoV, they can be used as a carrier to deliver foreign genes into such target cells as Vero E6, HFL 1, NCI-H520, A-549, or MRC-5 cells. They can also be used to introduce inhibitory RNAs into these host cells to treat the infection of SARS CoV.

Spike-GP64 Fusion Protein Targets Baculovirus to Mammalian Cells.

To trace whether the above-described recombinant baculovirus target and enter target cells pf SARS CoV, a sequence encoding EGFP was introduced into the baculoviruses using the above-described pTpcE plasmid and the AcMNPV/Sf21 cell line system. All the recombinant baculoviruses contained a green fluorescent protein gene driven by the cytomegalovirus immediate early promoter (CMV promoter). If the baculoviruses entered into cells, the cells would emit green fluorescent upon irradiation due to intracellular green fluorescent proteins expressed form the gene.

Vero E6 cells, known target of SARS CoV, were used in this experiment. The cells were grown at 37° C. in a minimum essential medium (MEM), supplemented with 10% FBS and 2% (v/v) penicillin-streptomycin solution (GIBCO BRL). All viral stocks were prepared according to the standard protocols described by O'Reilly et al. (1994, Baculovirus Expression Vectors: A Laboratory Manual, Oxford University Press, New York.). The virus titers were determined by quantitative PCR (Q-PCR) described in Lo et al., 2003, 4. Biotechnology Progress. Vero E6 cells grown in 35 mm culture dishes were infected with the baculovirus at moi of 100 and 10. More specifically, 1 ml MEM media containing recombinant baculovirus was added to each dish and rocked gently for 2 hours. Another milliliter of MEM medium was then added to each dish, and the cells were incubated at 37° C. incubator with 5% $CO_2$ for two days. The infected Vero E6 cells were then observed by confocal microscopy. It was found that no fluorescence was observed in the Vero E6 cells infected with spike protein-free recombinant baculovirus (vAtEG) upon irradiation. These results indicate that this wild-type baculovirus did not enter the Vero E6 cells.

The experiments were repeated with the baculoviruses vAtEG, vAtEGp64S510, vAtEGp64S763, and vAtEGp64S966, respectively. It was shown that vAtEGp64S763 and vAtEGp64S966 entered the Vero E6 cells efficiently. In contrast, vAtEG and vAtEGp64S510 did not.

The above-described experiments were further repeated except that HFL 1, NCI-H520, A-549, and MRC-5 cells were used. These cells, derived from the lung, are potential target cells for SARS CoV. Results similar to those for Vero E6 cells were obtained.

Antibody Neutralization Tests on Baculovirus Containing a Fusion of Spike Protein Antibody neutralization tests were conducted to examine whether anti-SARS CoV spike antibodies could neutralize the infection of Vero E6 cells by a recombinant baculovirus containing residues 510 to 763 of the spike protein. A rabbit antibody against the spike protein and two human antibodies that do not react with the spike protein were tested.

The above-described vAtEGp64S966 was used to generate baculovirus stocks. The stocks were incubated with different dilutions of the above-described antibodies for 1 hour at 37° C., respectively. A pre-immune serum was used as a negative control. Vero E6 cells were then infected with the incubated stocks and examined by confocal microscopy in the same manner described above.

It was found that the infection of the Vero E6 cells by the baculovirus was not influenced by the incubation with the human antibodies. In contrast, the infection was inhibited by the rabbit anti-spike antibody (up to 256× dilution). These results indicate that the just-described baculovirus can be used in neutralization test.

Drug Screening

The above described vAtEGp64S966 baculovirus was used to screen drugs. The baculovirus contains a spike protein driven by the polyhedrin promoter and a green fluorescent protein driven by the CMV promoter. Upon successful infection of the Vero E6 cells, the cells lit up under a fluorescent microscopy.

The baculoviruses were incubated with test compounds 0397 (Chloropromazine), 0643 (Prochlorperazine), 0646 (Promazine), 0649 (Propiomazine), 1016 (Triflupromazine), 2025 (Thioridazine), and 2121 (Clozapine), as well as DMSO (carrier, a negative control), respectively at various concentrations (1-33 μM) and then were examined for their ability to enter Vero E6 cells in the same manner described above. It was found that compounds 0643 (Prochlorperazine), 0649 (Propiomazine), and 2025 (Thioridazine) are very effective in blocking the entry. Indeed, some of these compounds were found to be able to block the infection of Vero E6 cells with SARS CoV. The results indicate that the recombinant baculovirus/Vero E6 cells system can be used to identify drugs for treating SARS RNA Interference To study whether small interference RNAs destroys SARS CoV, the replicase gene of the SARS CoV was fused to the GFP gene. Listed below is the RNA sequence encoding the replicase. Six segments, i.e., siRANs-1, 2, 3, 4, 5, and 6 (shown below and underlined; SEQ ID NOs: 13-18, respectively), were selected to make dsRNAs.

```
                                                                (SEQ ID NO:19)
   1 AUAUUAGGUU UUUACCUACC CAGGAAAAGC CAACCAACCU CGAUCUCUUG

51 UAGAUCUGUU CUCUAAACGA ACUUUAAAAU CUGUGUAGCU GUCGCUCGGC

101 UGCAUGCCUA GUGCACCUAC GCAGUAUAAA CAAUAAUAAA UUUUACUGUC

151 GUUGACAAGA AACGAGUAAC UCGUCCCUCU UCUGCAGACU GCUUACGGUU

201 UCGUCCGUGU UGCAGUCGAU CAUCAGCAUA CCUAGGUUUC GUCCGGGUGU

251 GACCGAAAGG UAAGAUGGAG AGCCUUGUUC UUGGUGUCAA CGAGAAAACA

301 CACGUCCAAC UCAGUUUGCC UGUCCUUCAG GUUAGAGACG UGCUAGUGCG
                       siRNA-1

351 UGGCUUCGGG GACUCUGUGG AAGAGGCCCU AUCGGAGGCA CGUGAACACC

401 UCAAAAAUGG CACUUGUGGU CUAGUAGAGC UGGAAAAAGG CGUACUGCCC
              siRNA-2

451 CAGCUUGAAC AGCCCUAUGU GUUCAUUAAA CGUUCUGAUG CCUUAAGCAC
                                          siRNA-3

501 CAAUCACGGC CACAAGGUCG UUGAGCUGGU UGCAGAAAUG GACGGCAUUC
                    siRNA-4*

551 AGUACGGUCG UAGCGGUAUA ACACUGGGAG UACUCGUGCC ACAUGUGGGC

601 GAAACCCCAA UUGCAUACCG CAAUGUUCUU CUUCGUAAGA ACGGUAAUAA
               siRNA-5                                siRNA-6*

651 GGGAGCCGGU GGUCAUAGCU AUGGCAUCGA UCUAAAGUCU UAUGACUUAG

701 GUGACGAGCU UGGCACUGAU CCCAUUGAAG AUUAUGAACA AAACUGGAAC

751 ACUAAGCAUG GCAGUGGUGC ACUCCGUGAA CUGACUCGUG AGCUCAAUGG

801 AGGUGCAGUC ACUCGCUAUG UCGACAACAA UUUCUGUGGC CCAGAUGGGU

851 ACCCUCUUGA UUGCAUCAAA GAUUUUCUCG CACGCGCGGG CAAGUCAAUG

901 UGCACUCUUU CCGAACAACU UGAUUACAUC GAGUCGAAGA GAGGUGUCUA

951 CUGCUGCCGU GACCAUGAGC AUGAAAUUGC CUGGUUCACU GAGCGCUCUG

1001 AUAAGAGCUA CGAGCACCAG ACACCCUUCG AAAUUAAGAG UGCCAAGAAA

1051 UUUGACACUU UCAAAGGGGA AUGCCCAAAG UUUGUGUUUC CUCUUAACUC

1101 AAAAGUCAAA GUCAUUCAAC CACGUGUUGA AAAGAAAAAG ACUGAGGGUU

1151 UCAUGGGGCG UAUACGCUCU GUGUACCCUG UUGCAUCUCC ACAGGAGUGU

1201 AACAAUAUGC ACUUGUCUAC CUUGAUGAAA UGUAAUCAUU GCGAUGAAGU

1251 UUCAUGGCAG ACGUGCGACU UCUGAAAGC CACUUGUGAA CAUUGUGGCA
```

```
1301 CUGAAAAUUU AGUUAUUGAA GGACCUACUA CAUGUGGGUA CCUACCUACU

1351 AAUGCUGUAG UGAAAAUGCC AUGUCCUGCC UGUCAAGACC CAGAGAUUGG

1401 ACCUGAGGAU AGUGUUGCAG AUUAUCACAA CCACUCAAAC AUUGAAACUC

1451 GACUCCGCAA GGGAGGUAGG A
```

A baculovirus containing this fusion gene, as well as a GP64-spike fusion protein, was generated in the manner described above. The virus was then used to infect Vero E6 cells, which were co-transfected with the above-described siRNAs 1-6.

Fluorescent emitted by GFP in the cells were then examined. It was shown several siRNAs effectively repressed the expression of the replicase-GFP fusion gene, as reflected by the lack of fluorescent. The results indicate that the recombinant baculovirus/Vero E6 cells system can be used to identify RNAi agent for treating SARS and that the recombinant baculoviruses of this invention are useful in delivering an anti-coronavirus agent into target cells in a patient.

EXAMPLE 2

In this example, influenza A virus (IAV) hemagglutinin was incorporated into a baculovirus in the manner described above.

An expression construct encoding fusion protein HA-gp64 was generated by linking the H5-HA extracellular domain onto the transmembrane and cytosolic domains of baculoviral gp64 protein. The signal peptide of HA was also replaced by gp64 signal peptide to target the fusion protein onto the surface of the recombinant baculovirus. The fusion gene was placed after the CMVie and p10 promoter sequences in the pTriEx-3 transfer vector (Novagen) with or without an additional gp64 promoter to generate pAtHscR and pAtgHscR plasmids. These two vectors also contained a $DsR_2$ reporter gene under the control of both SV40 and CMVm promoters, respectively, for expressing $dsR_2$ in insect, mammalian, or avian cells. A control vector containing just the $DsR_2$ expression cassette, pAtscR, was also constructed.

The just-described pAtHscR, pAtgHscR, and pAtscR vectors were respectively co-transfected with vAcRP23.Laz (PharMingen), a linearized viral DNA of AcMNPV, into Spodoptera frugiperda (Sf21) cells using Cellfectin (Life Technologies). End-point dilution was used to purify recombinant baculovirus clones, vAtscR, vAtgHscR, and vAtHscR. All viral stocks were prepared according to the standard protocols described by O'Reilly et al. Baculovirus Expression Vectors: A Laboratory Manual (1994) Oxford University Press, New York. The virus titers were determined by quantitative PCR (Q-PCR) described in Lo et al., 2004, Biotechnol. Prog. 20, 354.

Viral DNA was then extracted from the virus using the High Pure Viral Nucleic Acid Kit (Roche). HA-specific PCR primers were used to confirm the successful integration of HA-gp64 gene into the viral genome. Purified viral DNA served as templates in the viral DNA PCR, with HA-specific primers. A 1555 bp PCR product was detected in samples from all of the virus except vAtHscR. Western blotting experiment further confirmed the expression of HA-gp64 protein within insect Sf-21 and chicken/mammalian cells. These results indicate that that all the HA-containing recombinant baculoviruses contained the HA gene in their genome.

The above-described recombinant viruses were used to transduce both mammalian Vero E6 cells and chicken DF-1 cells by standard methods. The cells were then examined under a fluorescent microscope. The presence of $DsR_2$-specific fluorescence in a cell indicated that the cell was transduced by a recombinant virus and expressed the $DsR_2$ reporter gene.

It was found that the HA-displaying recombinant baculoviruses (i.e., vAtHscR and vAtgHscR) showed much greater abilities to enter the cells than the control vAtscR baculovirus. Also, the addition of gp64 promoter enhanced this ability, probably due to increased amount of HA-gp64 fusion protein on the surface of the recombinant baculovirus, as it was produced at the same time periods as the native gp64 protein. The virus was designed to also produce HA-gp64 fusion protein within the mammalian/avian cells through the CMVie promoter.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A recombinant baculovirus comprising a fusion heterologous polypeptide that contains a baculoviral envelope-targeting sequence, wherein the heterologous polypeptide is located on the surface of the baculovirus and the baculoviral envelope-targeting sequence consists of SEQ ID NO: 9.

2. The recombinant baculovirus of claim 1, wherein the heterologous polypeptide contains the sequence of a polypeptide of a heterologous virus.

3. The recombinant baculovirus of claim 2, wherein the heterologous virus is a coronavirus.

4. The recombinant baculovirus of claim 3, wherein the coronavirus virus is a severe acute respiratory syndrome coronavirus.

5. The recombinant baculovirus of claim 3, wherein the heterologous polypeptide contains the sequence of the envelope protein, membrane protein, nucleocapsid protein, or spike protein of the coronavirus, or an antigenic fragment thereof.

6. The recombinant baculovirus of claim 5, wherein the heterologous polypeptide contains one of SEQ ID NOs: 1-8, or an antigenic fragment thereof.

7. The recombinant baculovirus of claim 5, wherein the heterologous polypeptide contains the sequence of the spike protein of the coronavirus, or an antigenic fragment thereof.

8. The recombinant baculovirus of claim 7, wherein the heterologous polypeptide contains one of SEQ ID NOs: 5-8, or an antigenic fragment thereof.

9. The recombinant baculovirus of claim 2, wherein the heterologous peptide contains the extracellular domain sequence of hemagglutinin of an influenza virus.

10. The recombinant baculovirus of claim 9, wherein the heterologous polypeptide contains the extracellular domain sequence of hemagglutinin of an influenza A virus.

11. The recombinant baculovirus comprising a fusion heterologous polypeptide that contains a baculoviral envelope-targeting sequence or a functional equivalent thereof, wherein the heterologous polypeptide is located on the surface of the baculovirus and the baculoviral envelope-targeting sequence contains SEQ ID NO: 9, and wherein the heterologous polypeptide contains SEQ ID NO: 10.

12. A method of identifying a compound for treating an infection with a virus, the method comprising:
    incubating a first cell that binds to the virus and the recombinant baculovirus of claim 1 in a medium containing a compound; and
    determining a level of the binding between the first cell and the recombinant baculovirus,
    wherein the compound is determined to be effective in treating the infection if the level of the binding is lower than that determined in the same manner from a second cell except that the second cell is incubated in a medium free of the compound.

13. The recombinant baculovirus of claim 10, wherein the heterologous polypeptide contains SEQ ID NO: 10 or an antigenic fragment thereof.

* * * * *

SEQUENCE LISTING

```
<160> NUMBER OF SEQ ID NOS: 25

<210> SEQ ID NO 1
<211> LENGTH: 76
<212> TYPE: PRT
<213> ORGANISM: SARS coronavirus TW1
```

```
<400> SEQUENCE: 1

Met Tyr Ser Phe Val Ser Glu Glu Thr Gly Thr Leu Ile Val Asn Ser
 1               5                  10                  15

Val Leu Leu Phe Leu Ala Phe Val Val Phe Leu Leu Val Thr Leu Ala
                20                  25                  30

Ile Leu Thr Ala Leu Arg Leu Cys Ala Tyr Cys Cys Asn Ile Val Asn
                35                  40                  45

Val Ser Leu Val Lys Pro Thr Val Tyr Val Tyr Ser Arg Val Lys Asn
        50                  55                  60

Leu Asn Ser Ser Glu Gly Val Pro Asp Leu Leu Val
65                  70                  75

<210> SEQ ID NO 2
<211> LENGTH: 221
<212> TYPE: PRT
<213> ORGANISM: SARS coronavirus TW1

<400> SEQUENCE: 2

Met Ala Asp Asn Gly Thr Ile Thr Val Glu Glu Leu Lys Gln Leu Leu
 1               5                  10                  15

Glu Gln Trp Asn Leu Val Ile Gly Phe Leu Phe Leu Ala Trp Ile Met
                20                  25                  30

Leu Leu Gln Phe Ala Tyr Ser Asn Arg Asn Arg Phe Leu Tyr Ile Ile
                35                  40                  45

Lys Leu Val Phe Leu Trp Leu Leu Trp Pro Val Thr Leu Ala Cys Phe
        50                  55                  60

Val Leu Ala Ala Val Tyr Arg Ile Asn Trp Val Thr Gly Gly Ile Ala
65                  70                  75                  80

Ile Ala Met Ala Cys Ile Val Gly Leu Met Trp Leu Ser Tyr Phe Val
                85                  90                  95

Ala Ser Phe Arg Leu Phe Ala Arg Thr Arg Ser Met Trp Ser Phe Asn
                100                 105                 110

Pro Glu Thr Asn Ile Leu Leu Asn Val Pro Leu Arg Gly Thr Ile Val
                115                 120                 125

Thr Arg Pro Leu Met Glu Ser Glu Leu Val Ile Gly Ala Val Ile Ile
    130                 135                 140

Arg Gly His Leu Arg Met Ala Gly His Ser Leu Gly Arg Cys Asp Ile
145                 150                 155                 160

Lys Asp Leu Pro Lys Glu Ile Thr Val Ala Thr Ser Arg Thr Leu Ser
                165                 170                 175

Tyr Tyr Lys Leu Gly Ala Ser Gln Arg Val Gly Thr Asp Ser Gly Phe
                180                 185                 190

Ala Ala Tyr Asn Arg Tyr Arg Ile Gly Asn Tyr Lys Leu Asn Thr Asp
                195                 200                 205

His Ala Gly Ser Asn Asp Asn Ile Ala Leu Leu Val Gln
    210                 215                 220

<210> SEQ ID NO 3
<211> LENGTH: 422
<212> TYPE: PRT
<213> ORGANISM: SARS coronavirus TW1

<400> SEQUENCE: 3

Met Ser Asp Asn Gly Pro Gln Ser Asn Gln Arg Ser Ala Pro Arg Ile
 1               5                  10                  15

Thr Phe Gly Gly Pro Thr Asp Ser Thr Asp Asn Asn Gln Asn Gly Gly
```

-continued

```
                    20                  25                  30
Arg Asn Gly Ala Arg Pro Lys Gln Arg Pro Gln Gly Leu Pro Asn
             35                  40                  45
Asn Thr Ala Ser Trp Phe Thr Ala Leu Thr Gln His Gly Lys Glu
         50                  55                  60
Leu Arg Phe Pro Arg Gly Gln Gly Val Pro Ile Asn Thr Asn Ser Gly
 65                  70                  75                  80
Pro Asp Asp Gln Ile Gly Tyr Tyr Arg Arg Ala Thr Arg Arg Val Arg
                     85                  90                  95
Gly Gly Asp Gly Lys Met Lys Glu Leu Ser Pro Arg Trp Tyr Phe Tyr
                100                 105                 110
Tyr Leu Gly Thr Gly Pro Glu Ala Ser Leu Pro Tyr Gly Ala Asn Lys
            115                 120                 125
Glu Gly Ile Val Trp Val Ala Thr Glu Gly Ala Leu Asn Thr Pro Lys
        130                 135                 140
Asp His Ile Gly Thr Arg Asn Pro Asn Asn Asn Ala Ala Thr Val Leu
145                 150                 155                 160
Gln Leu Pro Gln Gly Thr Thr Leu Pro Lys Gly Phe Tyr Ala Glu Gly
                165                 170                 175
Ser Arg Gly Gly Ser Gln Ala Ser Ser Arg Ser Ser Arg Ser Arg
                180                 185                 190
Gly Asn Ser Arg Asn Ser Thr Pro Gly Ser Ser Arg Gly Asn Ser Pro
            195                 200                 205
Ala Arg Met Ala Ser Gly Gly Glu Thr Ala Leu Ala Leu Leu Leu
        210                 215                 220
Leu Asp Arg Leu Asn Gln Leu Glu Ser Lys Val Ser Gly Lys Gly Gln
225                 230                 235                 240
Gln Gln Gln Gly Gln Thr Val Thr Lys Lys Ser Ala Ala Glu Ala Ser
                245                 250                 255
Lys Lys Pro Arg Gln Lys Arg Thr Ala Thr Lys Gln Tyr Asn Val Thr
                260                 265                 270
Gln Ala Phe Gly Arg Arg Gly Pro Glu Gln Thr Gln Gly Asn Phe Gly
            275                 280                 285
Asp Gln Asp Leu Ile Arg Gln Gly Thr Asp Tyr Lys His Trp Pro Gln
290                 295                 300
Ile Ala Gln Phe Ala Pro Ser Ala Ser Ala Phe Phe Gly Met Ser Arg
305                 310                 315                 320
Ile Gly Met Glu Val Thr Pro Ser Gly Thr Trp Leu Thr Tyr His Gly
                325                 330                 335
Ala Ile Lys Leu Asp Asp Lys Asp Pro Gln Phe Lys Asp Asn Val Ile
            340                 345                 350
Leu Leu Asn Lys His Ile Asp Ala Tyr Lys Thr Phe Pro Pro Thr Glu
        355                 360                 365
Pro Lys Lys Asp Lys Lys Lys Thr Asp Glu Ala Gln Pro Leu Pro
    370                 375                 380
Gln Arg Gln Lys Lys Gln Pro Thr Val Thr Leu Leu Pro Ala Ala Asp
385                 390                 395                 400
Met Asp Asp Phe Ser Arg Gln Leu Gln Asn Ser Met Ser Gly Ala Ser
                405                 410                 415
Ala Asp Ser Thr Gln Ala
            420
```

<210> SEQ ID NO 4

<211> LENGTH: 1235
<212> TYPE: PRT
<213> ORGANISM: SARS coronavirus TW1

<400> SEQUENCE: 4

```
Met Phe Ile Phe Leu Leu Phe Leu Thr Leu Thr Ser Gly Ser Asp Leu
 1               5                  10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
370                 375                 380

Asp Ser Phe Val Val Lys Gly Asp Asp Val Arg Gln Ile Ala Pro Gly
```

-continued

```
            385                 390                 395                 400
Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
                420                 425                 430

Thr Gly Asn Tyr Asn Tyr Lys Tyr Arg Tyr Leu Arg His Gly Lys Leu
                435                 440                 445

Arg Pro Phe Glu Arg Asp Ile Ser Asn Val Pro Phe Ser Pro Asp Gly
                450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
                500                 505                 510

Pro Lys Leu Ser Thr Asp Leu Ile Lys Asn Gln Cys Val Asn Phe Asn
                515                 520                 525

Phe Asn Gly Leu Thr Gly Thr Gly Val Leu Thr Pro Ser Ser Lys Arg
                530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
                580                 585                 590

Glu Val Ala Val Leu Tyr Gln Asp Val Asn Cys Thr Asp Val Ser Thr
                595                 600                 605

Ala Ile His Ala Asp Gln Leu Thr Pro Ala Trp Arg Ile Tyr Ser Thr
                610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
                660                 665                 670

Ser Ile Val Ala Tyr Thr Met Ser Leu Gly Ala Asp Ser Ser Ile Ala
                675                 680                 685

Tyr Ser Asn Asn Thr Ile Ala Ile Pro Thr Asn Phe Ser Ile Ser Ile
                690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
                755                 760                 765

Gln Met Tyr Lys Thr Pro Thr Leu Lys Tyr Phe Gly Gly Phe Asn Phe
                770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815
```

```
Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
            885                 890                 895

Val Leu Tyr Glu Asn Gln Lys Gln Ile Ala Asn Gln Phe Asn Lys Ala
        900                 905                 910

Ile Ser Gln Ile Gln Glu Ser Leu Thr Thr Thr Ser Thr Ala Leu Gly
    915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Val Gln Ile Asp
            965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
        995                 1000                1005

Thr Lys Met Ser Glu Cys Val Leu Gly Gln Ser Lys Gly Val Val Phe
    1010                1015                1020

Leu His Val Thr Tyr Val Pro Ser Gln Glu Arg Asn Phe Thr Thr Ala
1025                1030                1035                1040

Pro Ala Ile Cys His Glu Gly Lys Ala Tyr Phe Pro Arg Glu Gly Val
            1045                1050                1055

Phe Val Phe Asn Gly Thr Ser Trp Phe Ile Thr Gln Arg Asn Phe Phe
        1060                1065                1070

Ser Pro Gln Ile Ile Thr Thr Asp Asn Thr Phe Val Ser Gly Asn Cys
    1075                1080                1085

Asp Val Val Ile Gly Ile Ile Asn Asn Thr Val Tyr Asp Pro Leu Gln
    1090                1095                1100

Pro Glu Leu Asp Ser Phe Lys Glu Glu Leu Asp Lys Tyr Phe Lys Asn
1105                1110                1115                1120

His Thr Ser Pro Asp Val Asp Leu Gly Asp Ile Ser Gly Ile Asn Ala
            1125                1130                1135

Ser Val Val Asn Ile Gln Lys Glu Ile Asp Arg Leu Asn Glu Val Ala
        1140                1145                1150

Lys Asn Leu Asn Glu Ser Leu Ile Asp Leu Gln Glu Leu Gly Lys Tyr
    1155                1160                1165

Glu Gln Tyr Ile Lys Trp Pro Trp Tyr Val Trp Leu Gly Phe Ile Ala
    1170                1175                1180

Gly Leu Ile Ala Ile Val Met Val Thr Ile Leu Leu Cys Cys Met Thr
1185                1190                1195                1200

Ser Cys Cys Ser Cys Leu Lys Gly Ala Cys Ser Cys Gly Ser Cys Cys
            1205                1210                1215

Lys Phe Asp Glu Asp Asp Ser Glu Pro Val Leu Lys Gly Val Lys Leu
            1220                1225                1230
```

His Tyr Thr
         1235

<210> SEQ ID NO 5
<211> LENGTH: 494
<212> TYPE: PRT
<213> ORGANISM: SARS coronavirus TW1

```
Asp Ser Phe Val Val Lys Gly Asp Val Arg Gln Ile Ala Pro Gly
    370                 375                 380

Gln Thr Gly Val Ile Ala Asp Tyr Asn Tyr Lys Leu Pro Asp Asp Phe
385                 390                 395                 400

Met Gly Cys Val Leu Ala Trp Asn Thr Arg Asn Ile Asp Ala Thr Ser
                405                 410                 415

Thr Gly Asn Tyr Asn Tyr Lys Tyr Arg Tyr Leu Arg His Gly Lys Leu
                420                 425                 430

Arg Pro Phe Glu Arg Asp Ile Ser Asn Val Pro Phe Ser Pro Asp Gly
            435                 440                 445

Lys Pro Cys Thr Pro Pro Ala Leu Asn Cys Tyr Trp Pro Leu Asn Asp
    450                 455                 460

Tyr Gly Phe Tyr Thr Thr Thr Gly Ile Gly Tyr Gln Pro Tyr Arg Val
465                 470                 475                 480

Val Val Leu Ser Phe Glu Leu Leu Asn Ala Pro Ala Thr Val
                485                 490

<210> SEQ ID NO 6
<211> LENGTH: 747
<212> TYPE: PRT
<213> ORGANISM: SARS coronavirus TW1

<400> SEQUENCE: 6

Asp Arg Cys Thr Thr Phe As

-continued

```
                245                 250                 255
Thr Asp Ala Val Asp Cys Ser Gln Asn Pro Leu Ala Glu Leu Lys Cys
            260                 265                 270
Ser Val Lys Ser Phe Glu Ile Asp Lys Gly Ile Tyr Gln Thr Ser Asn
            275                 280                 285
Phe Arg Val Val Pro Ser Gly Asp Val Val Arg Phe Pro Asn Ile Thr
            290                 295                 300
Asn Leu Cys Pro Phe Gly Glu Val Phe Asn Ala Thr Lys Phe Pro Ser
305                 310                 315                 320
Val Tyr Ala Trp Glu Arg Lys Lys Ile Ser Asn Cys Val Ala Asp Tyr
                325                 330                 335
Ser Val Leu Tyr Asn Ser Thr Phe Phe Ser Thr Phe Lys Cys Tyr Gly
            340                 345                 350
Val Ser Ala Thr Lys Leu Asn Asp Leu Cys Phe Ser Asn Val Tyr Ala
            355                 360                 365
Asp Ser Phe Val Val Lys Gly Asp Asp Val Arg Gln Ile Ala Pro Gly
            370                 375                 380
Gln Thr Gly Val Ile Ala Asp Tyr Asn Tyr Lys Leu Pro Asp Asp Phe
385                 390                 395                 400
Met Gly Cys Val Leu Ala Trp Asn Thr Arg Asn Ile Asp Ala Thr Ser
                405                 410                 415
Thr Gly Asn Tyr Asn Tyr Lys Tyr Arg Tyr Leu Arg His Gly Lys Leu
            420                 425                 430
Arg Pro Phe Glu Arg Asp Ile Ser Asn Val Pro Phe Ser Pro Asp Gly
            435                 440                 445
Lys Pro Cys Thr Pro Pro Ala Leu Asn Cys Tyr Trp Pro Leu Asn Asp
450                 455                 460
Tyr Gly Phe Tyr Thr Thr Thr Gly Ile Gly Tyr Gln Pro Tyr Arg Val
465                 470                 475                 480
Val Val Leu Ser Phe Glu Leu Leu Asn Ala Pro Ala Thr Val Cys Gly
                485                 490                 495
Pro Lys Leu Ser Thr Asp Leu Ile Lys Asn Gln Cys Val Asn Phe Asn
            500                 505                 510
Phe Asn Gly Leu Thr Gly Thr Gly Val Leu Thr Pro Ser Ser Lys Arg
            515                 520                 525
Phe Gln Pro Phe Gln Gln Phe Gly Arg Asp Val Ser Asp Phe Thr Asp
            530                 535                 540
Ser Val Arg Asp Pro Lys Thr Ser Glu Ile Leu Asp Ile Ser Pro Cys
545                 550                 555                 560
Ser Phe Gly Gly Val Ser Val Ile Thr Pro Gly Thr Asn Ala Ser Ser
                565                 570                 575
Glu Val Ala Val Leu Tyr Gln Asp Val Asn Cys Thr Asp Val Ser Thr
            580                 585                 590
Ala Ile His Ala Asp Gln Leu Thr Pro Ala Trp Arg Ile Tyr Ser Thr
            595                 600                 605
Gly Asn Asn Val Phe Gln Thr Gln Ala Gly Cys Leu Ile Gly Ala Glu
610                 615                 620
His Val Asp Thr Ser Tyr Glu Cys Asp Ile Pro Ile Gly Ala Gly Ile
625                 630                 635                 640
Cys Ala Ser Tyr His Thr Val Ser Leu Leu Arg Ser Thr Ser Gln Lys
                645                 650                 655
Ser Ile Val Ala Tyr Thr Met Ser Leu Gly Ala Asp Ser Ser Ile Ala
            660                 665                 670
```

```
Tyr Ser Asn Asn Thr Ile Ala Ile Pro Thr Asn Phe Ser Ile Ser Ile
            675                 680                 685

Thr Thr Glu Val Met Pro Val Ser Met Ala Lys Thr Ser Val Asp Cys
    690                 695                 700

Asn Met Tyr Ile Cys Gly Asp Ser Thr Glu Cys Ala Asn Leu Leu Leu
705                 710                 715                 720

Gln Tyr Gly Ser Phe Cys Thr Gln Leu Asn Arg Ala Leu Ser Gly Ile
            725                 730                 735

Ala Ala Glu Gln Asp Arg Asn Thr Arg Glu Val
        740                 745

<210> SEQ ID NO 7
<211> LENGTH: 950
<212> TYPE: PRT
<213> ORGANISM: SARS coronavirus TW1

<400> SEQUENCE: 7

Asp Arg Cys Thr Thr Phe Asp Asp Val Gln Ala Pro Asn Tyr Thr Gln
 1               5                  10                  15

His Thr Ser Ser Met Arg Gly Val Tyr Tyr Pro Asp Glu Ile Phe Arg
            20                  25                  30

Ser Asp Thr Leu Tyr Leu Thr Gln Asp Leu Phe Leu Pro Phe Tyr Ser
        35                  40                  45

Asn Val Thr Gly Phe His Thr Ile Asn His Thr Phe Gly Asn Pro Val
    50                  55                  60

Ile Pro Phe Lys Asp Gly Ile Tyr Phe Ala Ala Thr Glu Lys Ser Asn
65                  70                  75                  80

Val Val Arg Gly Trp Val Phe Gly Ser Thr Met Asn Asn Lys Ser Gln
            85                  90                  95

Ser Val Ile Ile Ile Asn Asn Ser Thr Asn Val Val Ile Arg Ala Cys
        100                 105                 110

Asn Phe Glu Leu Cys Asp Asn Pro Phe Phe Ala Val Ser Lys Pro Met
    115                 120                 125

Gly Thr Gln Thr His Thr Met Ile Phe Asp Asn Ala Phe Asn Cys Thr
130                 135                 140

Phe Glu Tyr Ile Ser Asp Ala Phe Ser Leu Asp Val Ser Glu Lys Ser
145                 150                 155                 160

Gly Asn Phe Lys His Leu Arg Glu Phe Val Phe Lys Asn Lys Asp Gly
            165                 170                 175

Phe Leu Tyr Val Tyr Lys Gly Tyr Gln Pro Ile Asp Val Val Arg Asp
        180                 185                 190

Leu Pro Ser Gly Phe Asn Thr Leu Lys Pro Ile Phe Lys Leu Pro Leu
    195                 200                 205

Gly Ile Asn Ile Thr Asn Phe Arg Ala Ile Leu Thr Ala Phe Ser Pro
210                 215                 220

Ala Gln Asp Ile Trp Gly Thr Ser Ala Ala Ala Tyr Phe Val Gly Tyr
225                 230                 235                 240

Leu Lys Pro Thr Thr Phe Met Leu Lys Tyr Asp Glu Asn Gly Thr Ile
            245                 250                 255

Thr Asp Ala Val Asp Cys Ser Gln Asn Pro Leu Ala Glu Leu Lys Cys
        260                 265                 270

Ser Val Lys Ser Phe Glu Ile Asp Lys Gly Ile Tyr Gln Thr Ser Asn
    275                 280                 285

Phe Arg Val Val Pro Ser Gly Asp Val Val Arg Phe Pro Asn Ile Thr
```

-continued

```
            290                 295                 300
Asn Leu Cys Pro Phe Gly Glu Val Phe Asn Ala Thr Lys Phe Pro Ser
305                 310                 315                 320

Val Tyr Ala Trp Glu Arg Lys Lys Ile Ser Asn Cys Val Ala Asp Tyr
                325                 330                 335

Ser Val Leu Tyr Asn Ser Thr Phe Phe Ser Thr Phe Lys Cys Tyr Gly
                340                 345                 350

Val Ser Ala Thr Lys Leu Asn Asp Leu Cys Phe Ser Asn Val Tyr Ala
                355                 360                 365

Asp Ser Phe Val Val Lys Gly Asp Asp Val Arg Gln Ile Ala Pro Gly
370                 375                 380

Gln Thr Gly Val Ile Ala Asp Tyr Asn Tyr Lys Leu Pro Asp Asp Phe
385                 390                 395                 400

Met Gly Cys Val Leu Ala Trp Asn Thr Arg Asn Ile Asp Ala Thr Ser
                405                 410                 415

Thr Gly Asn Tyr Asn Tyr Lys Tyr Arg Tyr Leu Arg His Gly Lys Leu
                420                 425                 430

Arg Pro Phe Glu Arg Asp Ile Ser Asn Val Pro Phe Ser Pro Asp Gly
                435                 440                 445

Lys Pro Cys Thr Pro Pro Ala Leu Asn Cys Tyr Trp Pro Leu Asn Asp
                450                 455                 460

Tyr Gly Phe Tyr Thr Thr Thr Gly Ile Gly Tyr Gln Pro Tyr Arg Val
465                 470                 475                 480

Val Val Leu Ser Phe Glu Leu Leu Asn Ala Pro Ala Thr Val Cys Gly
                485                 490                 495

Pro Lys Leu Ser Thr Asp Leu Ile Lys Asn Gln Cys Val Asn Phe Asn
                500                 505                 510

Phe Asn Gly Leu Thr Gly Thr Gly Val Leu Thr Pro Ser Ser Lys Arg
                515                 520                 525

Phe Gln Pro Phe Gln Gln Phe Gly Arg Asp Val Ser Asp Phe Thr Asp
                530                 535                 540

Ser Val Arg Asp Pro Lys Thr Ser Glu Ile Leu Asp Ile Ser Pro Cys
545                 550                 555                 560

Ser Phe Gly Gly Val Ser Val Ile Thr Pro Gly Thr Asn Ala Ser Ser
                565                 570                 575

Glu Val Ala Val Leu Tyr Gln Asp Val Asn Cys Thr Asp Val Ser Thr
                580                 585                 590

Ala Ile His Ala Asp Gln Leu Thr Pro Ala Trp Arg Ile Tyr Ser Thr
                595                 600                 605

Gly Asn Asn Val Phe Gln Thr Gln Ala Gly Cys Leu Ile Gly Ala Glu
                610                 615                 620

His Val Asp Thr Ser Tyr Glu Cys Asp Ile Pro Ile Gly Ala Gly Ile
625                 630                 635                 640

Cys Ala Ser Tyr His Thr Val Ser Leu Leu Arg Ser Thr Ser Gln Lys
                645                 650                 655

Ser Ile Val Ala Tyr Thr Met Ser Leu Gly Ala Asp Ser Ser Ile Ala
                660                 665                 670

Tyr Ser Asn Asn Thr Ile Ala Ile Pro Thr Asn Phe Ser Ile Ser Ile
                675                 680                 685

Thr Thr Glu Val Met Pro Val Ser Met Ala Lys Thr Ser Val Asp Cys
                690                 695                 700

Asn Met Tyr Ile Cys Gly Asp Ser Thr Glu Cys Ala Asn Leu Leu Leu
705                 710                 715                 720
```

```
Gln Tyr Gly Ser Phe Cys Thr Gln Leu Asn Arg Ala Leu Ser Gly Ile
                725                 730                 735

Ala Ala Glu Gln Asp Arg Asn Thr Arg Glu Val Phe Ala Gln Val Lys
            740                 745                 750

Gln Met Tyr Lys Thr Pro Thr Leu Lys Tyr Phe Gly Gly Phe Asn Phe
        755                 760                 765

Ser Gln Ile Leu Pro Asp Pro Leu Lys Pro Thr Lys Arg Ser Phe Ile
    770                 775                 780

Glu Asp Leu Leu Phe Asn Lys Val Thr Leu Ala Asp Ala Gly Phe Met
785                 790                 795                 800

Lys Gln Tyr Gly Glu Cys Leu Gly Asp Ile Asn Ala Arg Asp Leu Ile
                805                 810                 815

Cys Ala Gln Lys Phe Asn Gly Leu Thr Val Leu Pro Pro Leu Leu Thr
            820                 825                 830

Asp Asp Met Ile Ala Ala Tyr Thr Ala Ala Leu Val Ser Gly Thr Ala
        835                 840                 845

Thr Ala Gly Trp Thr Phe Gly Ala Gly Ala Ala Leu Gln Ile Pro Phe
    850                 855                 860

Ala Met Gln Met Ala Tyr Arg Phe Asn Gly Ile Gly Val Thr Gln Asn
865                 870                 875                 880

Val Leu Tyr Glu Asn Gln Lys Gln Ile Ala Asn Gln Phe Asn Lys Ala
                885                 890                 895

Ile Ser Gln Ile Gln Glu Ser Leu Thr Thr Thr Ser Thr Ala Leu Gly
            900                 905                 910

Lys Leu Gln Asp Val Val Asn Gln Asn Ala Gln Ala Leu Asn Thr Leu
        915                 920                 925

Val Lys Gln Leu Ser Ser Asn Phe Gly Ala Ile Ser Ser Val Leu Asn
    930                 935                 940

Asp Ile Leu Ser Arg Leu
945                 950

<210> SEQ ID NO 8
<211> LENGTH: 254
<212> TYPE: PRT
<213> ORGANISM: SARS coronavirus TW1

<400> SEQUENCE: 8

Val Cys Gly Pro Lys Leu Ser Thr Asp Leu Ile Lys Asn Gln Cys Val
1               5                   10                  15

Asn Phe Asn Phe Asn Gly Leu Thr Gly Thr Gly Val Leu Thr Pro Ser
            20                  25                  30

Ser Lys Arg Phe Gln Pro Phe Gln Gln Phe Gly Arg Asp Val Ser Asp
        35                  40                  45

Phe Thr Asp Ser Val Arg Asp Pro Lys Thr Ser Glu Ile Leu Asp Ile
    50                  55                  60

Ser Pro Cys Ser Phe Gly Gly Val Ser Val Ile Thr Pro Gly Thr Asn
65                  70                  75                  80

Ala Ser Ser Glu Val Ala Val Leu Tyr Gln Asp Val Asn Cys Thr Asp
                85                  90                  95

Val Ser Thr Ala Ile His Ala Asp Gln Leu Thr Pro Ala Trp Arg Ile
            100                 105                 110

Tyr Ser Thr Gly Asn Asn Val Phe Gln Thr Gln Ala Gly Cys Leu Ile
        115                 120                 125

Gly Ala Glu His Val Asp Thr Ser Tyr Glu Cys Asp Ile Pro Ile Gly
```

-continued

```
            130                 135                 140
Ala Gly Ile Cys Ala Ser Tyr His Thr Val Ser Leu Leu Arg Ser Thr
145                 150                 155                 160

Ser Gln Lys Ser Ile Val Ala Tyr Thr Met Ser Leu Gly Ala Asp Ser
                165                 170                 175

Ser Ile Ala Tyr Ser Asn Asn Thr Ile Ala Ile Pro Thr Asn Phe Ser
                180                 185                 190

Ile Ser Ile Thr Thr Glu Val Met Pro Val Ser Met Ala Lys Thr Ser
                195                 200                 205

Val Asp Cys Asn Met Tyr Ile Cys Gly Asp Ser Thr Glu Cys Ala Asn
                210                 215                 220

Leu Leu Leu Gln Tyr Gly Ser Phe Cys Thr Gln Leu Asn Arg Ala Leu
225                 230                 235                 240

Ser Gly Ile Ala Ala Glu Gln Asp Arg Asn Thr Arg Glu Val
                245                 250

<210> SEQ ID NO 9
<211> LENGTH: 302
<212> TYPE: PRT
<213> ORGANISM: Baculovirus GP64

<400> SEQUENCE: 9

Ser Met Ile Leu Lys Gln Lys Ser Thr Phe Thr Thr Arg Gln Ile Lys
1               5                   10                  15

Ala Ala Cys Leu Leu Ile Lys Asp Asp Lys Asn Asn Pro Glu Ser Val
                20                  25                  30

Thr Arg Glu His Cys Leu Ile Asp Asn Asp Ile Tyr Asp Leu Ser Lys
                35                  40                  45

Asn Thr Trp Asn Cys Lys Phe Asn Arg Cys Ile Lys Arg Lys Val Glu
            50                  55                  60

His Arg Val Lys Lys Arg Pro Pro Thr Trp Arg His Asn Val Arg Ala
65              70                  75                  80

Lys Tyr Thr Glu Gly Asp Thr Ala Thr Lys Gly Asp Leu Met His Ile
                85                  90                  95

Gln Glu Glu Leu Met Tyr Glu Asn Asp Leu Leu Lys Met Asn Ile Glu
                100                 105                 110

Leu Met His Ala His Ile Asn Lys Leu Asn Asn Met Leu His Asp Leu
            115                 120                 125

Ile Val Ser Val Ala Lys Val Asp Glu Arg Leu Ile Gly Asn Leu Met
                130                 135                 140

Asn Asn Ser Val Ser Ser Thr Phe Leu Ser Asp Asp Thr Phe Leu Leu
145                 150                 155                 160

Met Pro Cys Thr Asn Pro Pro Ala His Thr Ser Asn Cys Tyr Asn Asn
                165                 170                 175

Ser Ile Tyr Lys Glu Gly Arg Trp Val Ala Asn Thr Asp Ser Ser Gln
                180                 185                 190

Cys Ile Asp Phe Arg Asn Tyr Lys Glu Leu Ala Ile His Asp Val Glu
            195                 200                 205

Phe Trp Ile Pro Thr Ile Gly Asn Thr Thr Tyr His Asp Ser Trp Lys
            210                 215                 220

Asp Ala Ser Gly Trp Ser Phe Ile Ala Gln Gln Lys Ser Asn Leu Ile
225                 230                 235                 240

Thr Thr Met Glu Asn Thr Lys Phe Gly Gly Val Gly Thr Ser Leu Ser
                245                 250                 255
```

-continued

```
Asp Ile Thr Ser Met Ala Glu Gly Glu Leu Ala Ala Lys Leu Thr Ser
            260                 265                 270

Phe Met Phe Gly His Val Val Asn Phe Val Ile Ile Leu Ile Val Ile
        275                 280                 285

Leu Phe Leu Tyr Cys Met Ile Arg Asn Arg Asn Arg Gln Tyr
    290                 295                 300

<210> SEQ ID NO 10
<211> LENGTH: 563
<212> TYPE: PRT
<213> ORGANISM: Influenza A virus

<400> SEQUENCE: 10

Met Gly Lys Ile Val Leu Phe Leu Ser Ile Ala Ser Leu Val Asn Ser
1               5                   10                  15

Asp Lys Ile Cys Ile Gly Tyr His Ala Asn Asn Ser Thr Ala Lys Val
            20                  25                  30

Asp Thr Ile Met Glu Lys Asn Val Thr Val Thr His Ala Lys Asp Ile
        35                  40                  45

Pro Glu Lys Lys His Asn Gly Lys Leu Cys Gly Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Met Val Pro Glu Trp Ser Tyr Ile Val
                85                  90                  95

Glu Lys Asn Asn Pro Val Asn Gly Leu Cys Tyr Pro Gly Asp Phe Gln
            100                 105                 110

Asp Tyr Glu Glu Leu Lys His Leu Leu Ser Ser Thr Thr His Phe Glu
        115                 120                 125

Lys Ile Gln Met Phe Pro Arg Asn Ser Trp Pro Gln His Asp Thr Ser
    130                 135                 140

Gly Val Thr Ala Ala Cys Pro Phe Asn Gly Lys Ser Ser Phe Phe Arg
145                 150                 155                 160

Asn Met Val Trp Leu Ile Lys Lys Asn Asn Glu Tyr Leu Thr Ile Lys
                165                 170                 175

Arg Gly Tyr Lys Asn Thr Asn Gln Glu Asp Leu Leu Ile Met Trp Gly
            180                 185                 190

Ile His His Pro Ser His Asp Glu Glu Gln Val Arg Leu Tyr Lys Asn
        195                 200                 205

Pro Arg Thr Tyr Ile Ser Val Gly Thr Ser Thr Leu Asn Gln Arg Leu
    210                 215                 220

Ser Pro Ile Ile Ala Glu Arg Pro Gln Val Asn Gly Gln Ser Gly Arg
225                 230                 235                 240

Met Ser Phe Tyr Trp Thr Ile Leu Lys Pro Ser Asp Thr Ile Asn Phe
                245                 250                 255

Glu Thr Asn Gly Asn Phe Ile Pro Pro Glu Tyr Ala Phe Lys Ile Val
            260                 265                 270

Lys Lys Gly Asp Ser Ala Ile Ile Arg Ser Glu Leu Glu Tyr Gly Asn
        275                 280                 285

Cys Asn Thr Arg Cys Gln Thr Pro Met Gly Ala Leu Asn Ser Ser Met
    290                 295                 300

Pro Phe Gln Asn Ile His Pro Ile Thr Ile Gly Glu Cys Pro Lys Tyr
305                 310                 315                 320

Val Lys Ser Asn Arg Leu Val Leu Ala Thr Gly Leu Arg Asn Ile Pro
                325                 330                 335
```

-continued

Gln Ile Glu Thr Arg Gly Leu Phe Gly Ala Ile Ala Gly Phe Ile Glu
            340                 345                 350
Gly Gly Trp Gln Gly Met Val Asp Gly Trp Tyr Gly Tyr His His Ser
        355                 360                 365
Asn Asp Gln Gly Ser Gly Tyr Ala Ala Asp Lys Glu Ser Thr Gln Arg
    370                 375                 380
Ala Ile Asp Gly Ile Thr Asn Lys Val Asn Ser Ile Ile Asp Lys Met
385                 390                 395                 400
Asn Thr Gln Phe Glu Ala Val Gly Lys Glu Phe Asn Asn Leu Glu Arg
                405                 410                 415
Arg Ile Gly Asn Leu Asn Lys Lys Met Glu Asp Gly Phe Leu Asp Ile
            420                 425                 430
Trp Thr Tyr Asn Ala Glu Leu Leu Val Leu Met Glu Asn Glu Arg Thr
        435                 440                 445
Leu Asp Leu His Asp Ser Asn Val Lys Asn Leu Tyr Glu Lys Val Arg
    450                 455                 460
Leu Gln Leu Lys Asp Asn Ala Lys Glu Leu Gly Asn Gly Cys Phe Glu
465                 470                 475                 480
Phe His His Lys Cys Asp Asn Glu Cys Met Glu Ser Val Lys Asn Gly
                485                 490                 495
Thr Tyr Asn Tyr Pro His Tyr Ser Glu Glu Ala Arg Leu Lys Arg Glu
            500                 505                 510
Glu Ile Ser Gly Val Lys Leu Glu Ser Ile Gly Thr Tyr Gln Ile Leu
        515                 520                 525
Ser Ile Tyr Ser Thr Val Ala Ser Ser Leu Val Leu Ala Ile Met Ile
    530                 535                 540
Ala Gly Leu Ser Phe Trp Met Cys Ser Asn Gly Ser Leu Gln Cys Arg
545                 550                 555                 560
Ile Cys Ile

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
aggcctcaat gctactagta aatc                                      24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
ggccgcaaag gccgaatgcg ccgc                                      24

<210> SEQ ID NO 13
<211> LENGTH: 21
<212> TYPE: RNA
<213> ORGANISM: SARS coronavirus

<400> SEQUENCE: 13
aacucaguuu gccuguccuu c                                         21

```
<210> SEQ ID NO 14
<211> LENGTH: 21
<212> TYPE: RNA
<213> ORGANISM: SARS coronavirus

<400> SEQUENCE: 14
aaauggcacu ugggucuag u                                               21

<210> SEQ ID NO 15
<211> LENGTH: 21
<212> TYPE: RNA
<213> ORGANISM: SARS coronavirus

<400> SEQUENCE: 15
aaacguucug augccuuaag c                                              21

<210> SEQ ID NO 16
<211> LENGTH: 21
<212> TYPE: RNA
<213> ORGANISM: SARS coronavirus

<400> SEQUENCE: 16
aaggucguug agcugguugc a                                              21

<210> SEQ ID NO 17
<211> LENGTH: 21
<212> TYPE: RNA
<213> ORGANISM: SARS coronavirus

<400> SEQUENCE: 17
aaaccccaau ugcauaccgc a                                              21

<210> SEQ ID NO 18
<211> LENGTH: 21
<212> TYPE: RNA
<213> ORGANISM: SARS coronavirus

<400> SEQUENCE: 18
aagaacggua auaagggagc c                                              21

<210> SEQ ID NO 19
<211> LENGTH: 1471
<212> TYPE: RNA
<213> ORGANISM: SARS coronavirus

<400> SEQUENCE: 19
auauuagguu uuuaccuacc caggaaaagc caaccaaccu cgaucucuug uagaucuguu      60
cucuaaacga acuuuaaaau cuguguagcu gucgcucggc ugcaugccua ugcaccuac      120 gcaguauaaa caauaauaaa uuuuacuguc guugacaaga aacgaguaac ucgucccucu      180
ucugcagacu gcuacgguu cgucgugu ugcagucgau caucagcaua ccuagguuuc       240 guccggugu gaccgaaagg uaagauggag agccuguuc uuggugucaa cgagaaaaca      300
cacguccaac ucaguuugcc uguccuucag guuagacg ugcuagugcg uggcuucggg      360
gacucugugg aagaggcccu aucggaggca cgugaacacc ucaaaaaugg cacuuggu      420 cuaguagagc uggaaaaagg cguacugccc cagcuugaac agcccuaugu guucauuaaa      480
cguucugaug ccuuaagcac caaucacggc cacaaggucg uugagcuggu ugcagaaaug      540
gacggcauuc aguacgguuc uagcgguaua acacgggag uacucugcc acauggggc       600 gaaacccccaa uugcauaccg caauguucuu cuucguaaga acgguaauaa gggagccggu      660
```

```
ggucauagcu auggcaucga ucuaaagucu uaugacuuag gugacgagcu uggcacugau      720
cccauugaag auuaugaaca aaacuggaac acuaagcaug gcaguggugc acuccgugaa      780
cucacucgug agcucaaugg aggugcaguc acucgcuaug ucgacaacaa uuucuguggc      840
ccagaugggu acccucuuga uugcaucaaa gauuuucucg cacgcgcggg caagucaaug      900
ugcacucuuu ccgaacaacu ugauuacauc gagucgaaga gaggugucua cugcugccgu      960
gaccaugagc augaaauugc cugguucacu gagcgcucug auaagagcua cgagcaccag     1020
acacccuucg aaauuaagag ugccaagaaa uuugacacuu ucaagggga augcccaaag     1080 uuuguguuuc cucuuaacuc aaaagucaaa gucauucaac cacguguuga aagaaaaag     1140 acugagqquu ucauggqqcg uauacgcucu guguacccug uugcaucucc acaggagugu     1200
aacaauaugc acuugucuac cuugaugaaa uguaaucauu gcgaugaagu ucauggcag     1260 acgugcgacu uucugaaagc cacuugugaa cauuguggca cugaaaauuu aguuauugaa     1320
ggaccuacua caugggqua ccaccuacu aaugcuguag ugaaaaugcc auguccugcc     1380
ugucaagacc cagagauugg accugagcau aguguugcag auuaucacaa ccacucaaac     1440
auugaaacuc gacuccgcaa gggagguagg a                                    1471

<210> SEQ ID NO 20
<211> LENGTH: 32
<212> TYPE: DNA
<213> ORGANISM: Artificial Sequence
<220> FEATURE:
<223> OTHER INFORMATION: Primer

<400> SEQUENCE: 20
ggccacggtg gccatgattc tcaaacaaaa gt                                    32

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
cccgggttaa tattgtctat tacg                                             24

<210> SEQ ID NO 22
<211> LENGTH: 32
<212> TYPE: DNA
<213> ORGANISM: Artificial Sequence
<220> FEATURE:
<223> OTHER INFORMATION: Primer

<400> SEQUENCE: 22
ggcctttgcg gccgaccggt gcaccacttt tg                                    32

<210> SEQ ID NO 23
<211> LENGTH: 27
<212> TYPE: DNA
<213> ORGANISM: Artificial Sequence
<220> FEATURE:
<223> OTHER INFORMATION: Primer

<400> SEQUENCE: 23
ggccaccgtg gccggtgcat ttaaaag                                          27

<210> SEQ ID NO 24
```

```
<211> LENGTH: 33
<212> TYPE: DNA
<213> ORGANISM: Artificial Sequence
<220> FEATURE:
<223> OTHER INFORMATION: Primer

<400> SEQUENCE: 24
ggccaccgtg gccacttcac gtgtgttgcg atc                          33

<210> SEQ ID NO 25
<211> LENGTH: 39
<212> TYPE: DNA
<213> ORGANISM: Artificial Sequence
<220> FEATURE:
<223> OTHER INFORMATION: Primer

<400> SEQUENCE: 25
ggccaccgtg gccagtcgcg aaaggatgtc atttagcac                    39
```